(12) United States Patent
Glazer (10) Patent No.: US 8,715,292 B2
(45) Date of Patent: May 6, 2014

(54) HAND HELD INTEGRATED PEDICLE SCREW PLACEMENT DEVICE

(76) Inventor: Paul Andrew Glazer, Chestnut Hill, MA (US)

( * ) Notice: Subject to any disclaimer, the term of this patent is extended or adjusted under 35 U.S.C. 154(b) by 1303 days.

(21) Appl. No.: 11/662,395

(22) PCT Filed: Sep. 15, 2005

(86) PCT No.: PCT/US2005/033024
§ 371 (c)(1),
(2), (4) Date: Feb. 13, 2008

(87) PCT Pub. No.: WO2006/036584
PCT Pub. Date: Apr. 6, 2006

(65) Prior Publication Data
US 2008/0195102 A1 Aug. 14, 2008

Related U.S. Application Data

(60) Provisional application No. 60/609,819, filed on Sep. 15, 2004.

(51) Int. Cl.
*A61B 17/56* (2006.01)
(52) U.S. Cl.
USPC .......................................... 606/96; 600/424
(58) Field of Classification Search
USPC ................. 600/130, 424; 606/96, 98, 104
See application file for complete search history.

(56) References Cited

U.S. PATENT DOCUMENTS

| 5,640,960 | A  | * | 6/1997  | Jones et al. ................ 600/453 |
| 6,416,518 | B1 | * | 7/2002  | DeMayo ...................... 606/96 |
| 6,450,271 | B1 | * | 9/2002  | Tibbitts et al. .............. 175/374 |
| 6,491,635 | B1 | * | 12/2002 | Mazess et al. ............... 600/449 |
| 6,849,047 | B2 |   | 2/2005  | Goodwin |
| 2003/0078495 | A1 | * | 4/2003 | Goodwin ...................... 600/424 |
| 2003/0187348 | A1 |   | 10/2003 | Goodwin |
| 2004/0034355 | A1 | * | 2/2004 | Govari et al. ................. 606/72 |
| 2005/0070916 | A1 | * | 3/2005 | Hollstien et al. ............. 606/96 |

FOREIGN PATENT DOCUMENTS

| DE | 199 21 279 C1 | 11/2000 |
| FR | 2 856 577 A | 12/2004 |
| WO | WO 2005/000124 | 1/2005 |

\* cited by examiner

*Primary Examiner* — Christian Sevilla
(74) *Attorney, Agent, or Firm* — Edwards Wildman Palmer LLP; Joshua L. Jones; Scott D. Wofsy

(57) ABSTRACT

A device for applying a medical element has a housing defining a longitudinal axis with a channel disposed therethrough. The housing has a proximal and a distal opening. The device also has at least one sensing device positioned adjacent to the distal opening. The device also has a signaling device disposed adjacent the housing. The at least one sensing device interrogates a bone location for one or more variables of the bone location as the device is moved over the bone location. The at least one sensing devices outputs a signal to the device and the signaling device signals an identification of a homogenous bone region. The medical element is applied to the homogenous bone location coaxially from the proximal opening through the channel and through the distal opening without removal of the device from the homogenous bone region.

20 Claims, 4 Drawing Sheets

HAND HELD INTEGRATED PEDICLE SCREW PLACEMENT DEVICE

CROSS REFERENCE TO RELATED PATENT APPLICATIONS

The present application claims the benefit of and priority to International Application No. PCT/US2005/033024 filed Sep. 15, 2005, claiming priority from U.S. Provisional Application Ser. No. 60/609,819 filed Sep. 15, 2004, the entire contents of each of which are incorporated herein by reference.

BACKGROUND

The present disclosure relates to a hand held device for the application of one or more pedicle screws. More particularly, the present disclosure relates to a hand held device with at least one ultrasonic transducer element to identify a homogenous bone region for the application of the pedicle screws.

Current devices for placing pedicle screws have a number of limitations. Typically, in surgery, a surgeon will take a number of pre-operative fluoroscopic images. These fluoroscopic images will correctly show an area of interest and allow the surgeon to identify one or more areas for which to apply pedicle screws. Such fluoroscopic images or even radiographic images can provide a static picture of the region and show relevant structure of the bone. Such structures typically show voids, boundaries (between different types of bone) and fractures. The images also show homogenous bone regions. However, during the surgical procedure such treatment areas are difficult to visualize. Subsequent bone growth, and the change of positioning of the patient from when the images where taken and other features of the surgical area may obscure relevant structures of interest, and specifically the pedicle. Difficulties in such placement may result in or one or more detriments to the overall productivity of the surgical procedure.

The pedicle is a dense so-called "stem like" bone structure that projects from the posterior of the vertebra. There exist two such pedicles per vertebra that connect to other structures. The pedicle connects to other structures such as the vertebra arch and the lamina. Movement of the patient at surgery can alter the perception of the positioning of the bone features relative to an orientation of the images that were taken in a preoperative time frame. Often a surgeon must inject a marker to provide a reference point in the images.

Another approach uses computer imaging and/or x-ray imaging to provide some knowledge of the bony structure and the region of any possible voids, or the location of any fractures, or other structures. However, all of these imaging techniques are deficient because they provide static images without any real time feedback. All of these imaging techniques require a surgeon to examine the image, and then translate the positioning from the image to the corresponding bone region at the operative site. Once the desired location is found for a proper placement of a pedicle screw or other implant, the surgeon will often apply a titanium pedicle screw through the bone region to correct deformities and treat trauma.

Such screws may also be provided to immobilize the bone, and/or affix plates and rods to the spine. Although pedicle screws are most often used in the lumbar or lumbosacral spine, they can be also implanted in the thoracic spine, cervical spine and sacral vertebrae. The surgeon uses the pre-operative fluoroscopy or conventional x-ray images to determine the depth and angle for pedicle screw placement. A receiving channel is drilled and the pedicle screw is inserted. This practice of locating the region of interest can be time consuming and detract from the overall productivity of the operation. Moreover, as the surgical procedure necessitates that pedicle screws are introduced in relatively smaller sized bones, the positioning then becomes more difficult. Such positioning requires an experienced surgeon and time.

One such solution in the art is U.S. Pat. No. 6,849,047 to Goodwin (hereinafter "Goodwin"). Goodwin recites an apparatus for measuring one or more characteristics of bone using a transducer and a receiver. The apparatus is bulky and is rolled in on rollers to the operating room. The apparatus has an articulating arm. The apparatus further has a small test drill bit with a transducer. The transducer is passed in a lumen of the hollow test drill bit, and is used to inspect and monitor differences in acoustical impedance as the transducer is passed through a region in the bone. Goodwin is deficient as it monitors differences in acoustical impedance during drilling by the hollow test drill bit. Such a test application is deficient, may unduly weaken the bone and may lessen the integrity of the bone. Alternatively, Goodwin discloses that the transducer may be used to determine an initial starting location. However, once the initial starting location is determined, the transducer would have to be removed. This removal causes the surgeon to remove the apparatus, and then orient the drill on the determined site at a later time in order to commence drilling.

Accordingly, there is a need in the art for a real time positioning solution to determine proper pedicle screw placement. There is also a need for a solution that determines a region of interest and allows for simultaneously application of the pedicle screw. There is also a need for a device that does not require the surgeon to unduly consult pre-operative images, and then translate information from a static image to a dynamic site. There is a further need in the art for a hand held device that is comfortable to hold and that signals a surgeon that a homogeneous bone region has been located at the precise location of the homogeneous bone region. There is also a need in the art for a hand held and real time ultrasonic surgical device that can interrogate an area to determine the location of the homogenous bone region.

SUMMARY

According to an aspect of the present disclosure there is provided a device for applying a medical element. The device has a housing defining a longitudinal axis with a channel disposed therethrough. The housing has a proximal and a distal opening. The device also has at least one sensing device positioned adjacent to the distal opening. The device also has a signaling device disposed adjacent the housing. The at least one sensing device interrogates a bone location for one or more variables of the bone location as the device is moved over the bone location. The at least one sensing device outputs a signal to the device and the signaling device signals an identification of a homogenous bone region. The medical element is applied to the homogenous bone location coaxially from the proximal opening through the channel and through the distal opening without removal of the device from the homogenous bone region.

According to another aspect of the present disclosure there is provided a device for applying a medical element. A device has a housing defining a longitudinal axis with a channel being disposed therethrough. The housing has a proximal opening and a distal opening and at least one sensing device positioned adjacent the distal opening. The device has a controller disposed in or on the housing and the at least one sensing device interrogates a bone location for one or more variables of the bone at the bone location as the device is moved over the bone location or angled with respect to the bone location. The device has a controller that controls a transmitter to output a wireless signal to a receiver. The receiver is connected to a display unit. The display unit displays data that bears a predetermined relationship to an identification of a homogenous bone region suitably for receiving a pedicle screw or other medical implant. The display may be an image of the bone or any other suitable representation correlating the quality of bone in the direction of orientation of the sensing device for a desired distance extending from the distal end of the sensing device once the desired orientation of the sensing device is determined. The medical element is applied to the homogenous bone region coaxially from the proximal opening through the channel and through the distal opening without removal of the device from the homogenous bone region.

According to another aspect of the present disclosure there is provided a device for applying a medical element. The device has a housing defining a longitudinal axis and a channel being disposed therethrough. The housing having a proximal and a distal opening and at least one sensing device positioned adjacent the distal opening and a signaling device disposed adjacent the housing. The device also has the at least one sensing device interrogating a bone location for one or more variables of the bone at the bone location as the device is moved over the bone location or angled with respect to the bone. The at least one sensing device outputs a signal to the signaling device and the signaling device signals an identification of a homogenous bone region. The medical element is applied to the homogenous bone region coaxially from the proximal opening through the channel and through the distal opening without removal of the device from the homogenous bone region. The housing further comprises a surface treatment with the surface treatment being disposed in or on an inner surface of the channel.

According to still yet another aspect of the present disclosure there is provided a device for applying a medical element. The device has a housing defining a longitudinal axis with a channel being disposed therethrough with the housing having a proximal and a distal opening and at least one sensing device and a transceiver being positioned adjacent the housing, and preferably adjacent the distal opening. The at least one sensing device interrogates a bone location for one or more variables of the bone location as the device is moved over the bone location, or angled with respect thereto and the at least one sensing device outputs a signal to the transceiver. The signal bears a predetermined relationship to an identification of a homogenous bone region and the medical element is applied to the homogenous bone region coaxially from the proximal opening through the channel and through the distal opening without removal of the device from the homogenous bone region and is configured to form a pedicular channel.

According to another aspect of the present disclosure there is provided a method of performing surgery. The method has the steps of interrogating tissue using a cannulated device, identifying a suitable trajectory to insert a medical element into the tissue using the cannulated device and inserting the medical element through the cannulated device. According to yet another aspect of the present disclosure there is provided a method of performing surgery. The method has the steps of interrogating tissue using a cannulated device and sensing a parameter of the tissue. The method also has the steps of identifying a suitable trajectory and a suitable medical element insertion location from at least the sensed parameter, and inserting the medical element through the cannulated device at the location and at the trajectory. Other objects and features of the present disclosure will become apparent from consideration of the following description taken in conjunction with the accompanying drawings.

BRIEF DESCRIPTION OF THE DRAWINGS

By way of example only, embodiments of the pedicle screw placement unit of the present disclosure will be described with reference to the accompanying drawings, in which.

DETAILED DESCRIPTION

Detailed embodiments of the presently disclosed instruments, devices and systems will now be described in detail with reference to the drawing figures wherein like reference numerals identify similar or identical elements. In the drawings and in the description which follows, the term "proximal", as is traditional, will refer to the end of the instrument, device and/or system which is closest to the operator while the term "distal" will refer to the end of the instrument, device and/or system which is furthest from the operator.

Figure 1:
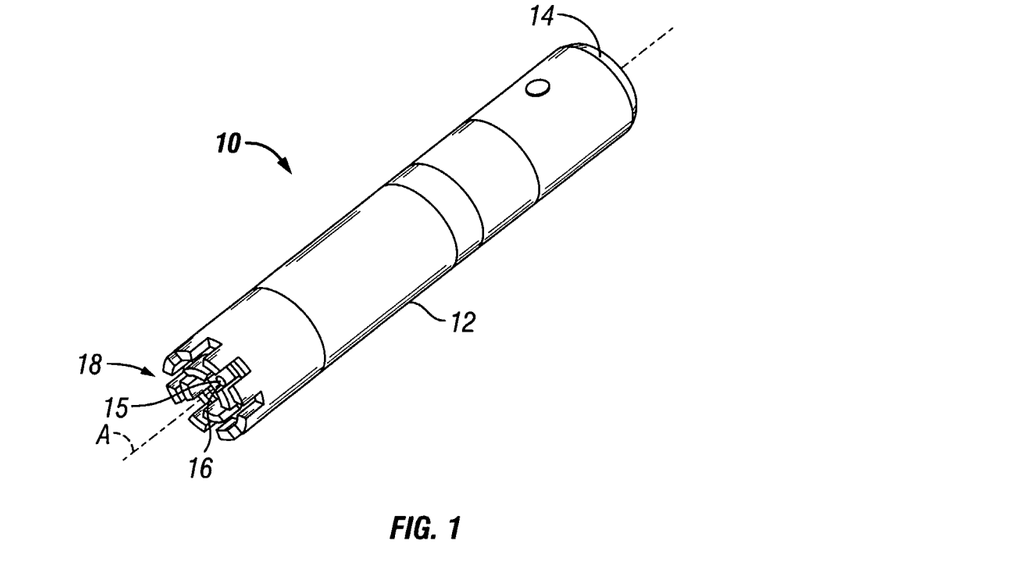
FIG. 1 is a perspective view of a hand held pedicle screw placement unit to identify a homogenous bone region according to an embodiment of the present disclosure.

Referring to FIG. 1, a pedicle screw placement unit, according to an embodiment of the present disclosure, is shown generally as 10. The pedicle screw placement unit 10 generally includes a housing 12. The housing 12 is a generally cylindrical shaped member. However, one skilled in the art should appreciate that the housing 12 is in no way limited to such a cylindrical arrangement and may be rectangular, oblong or in any shape known in the art to be comfortably gripped by a surgeon's hand with easy. The pedicle screw placement unit 10 has two discrete functions. First, the pedicle screw placement unit 10 identifies a homogenous bone region, or a solid bone region that can best hold a pedicle screw for a long period of time without fracturing or without any fracture. The unit 10 identifies the desired bone region and generates a signal locally on the unit 10 or alternatively generates a signal remote from the unit 10. The unit 10 most notably can identify the desired homogenous bone region in real time without generating of three dimensional images and without any bulky display devices that can impede the compact manner of the unit 10. Although being discussed in the context of pedicle screws, the present disclosure may be used in other procedures such as for trauma and reconstructive surgery and is in no way limited in any way to the spine or pedicle.

Often in pedicular cannulation surgery there exist two types of notably encountered bone types. First, there is a cortical bone and second, cancellous bone. The cortical bone is notably a dense and a hard bone covering. The cancellous bone makes up the so called "spongy and soft regions" on the inside of the bone. A successful procedure involves when a channel is created in the cancellous bone without any fracture of the hard bone covering or the cortical bone. A fracture is strongly disfavored and will greatly affect the productivity of the procedure, and is to be avoided. However, when there are no clear boundaries between a thick cortical wall and a core of cancellous bone, the surgeon's tactile feedback of the area may notably decrease. In this instance, the surgeon must rely on preoperative images. It has been observed that as the surgeon relies on the preoperative images and data, a risk of fracture may increase. The pedicle screw placement unit 10 will thus identify a homogenous bone region and related structures and provide an identification to a surgeon that the homogenous bone region has been found. The pedicle screw placement unit 10 will then allow the surgeon to apply a medical element such as a Kirschner wire coaxially through the unit 10 to the homogenous bone region without removal of the pedicle screw placement unit 10 and thus avoids any fracture. Advantageously, the pedicle screw would then be placed over the "K" wire after insertion.

Referring now to FIG. 1, there is shown a perspective view of the hand held pedicle screw placement unit 10. Notably, the unit 10 has a proximal opening 14 and a distal opening 16 with a channel 15 being disposed through the housing 12 or parallel to a longitudinal axis A of the unit 10. Generally, as shown the hand held pedicle screw placement unit 10 has a generally circular proximal opening 14 and a circular distal opening 16. However one skilled in the art should appreciate that the proximal and distal openings 14, 16 may have any shape in the art suitable for a coaxial insertion of medical elements such as a Kirschner wire through the channel 15 of the unit 10 as will be discussed herein.

The pedicle screw placement unit 10 has at least one sensor 18. In another embodiment, the unit 10 may have a number of sensors 18. In one embodiment, the sensors 18 are a number of ultrasonic transducer elements. The number of ultrasonic transducer elements 18 are intended to determine a suitable mass of homogenous bone to identify a region for the placement of a pedicle screw or similar surgical implant. The ultrasonic transducer elements 18 may be any device that converts electrical signals from the unit 10 to mechanical vibrations and also receives high frequency pressure pulses and converts the pulses to electrical signals.

In one embodiment, each of the ultrasonic transducer elements 18 is a piezoelectric ultrasonic transducer. Alternatively, the ultrasonic transducer elements 18 may be any device that generates and detects ultrasonic energy. Notably, the present disclosure can sense and determine distances to a boundary and then output a signal without any production of full scale images that may compromise the compact size of the unit 10. Preferably, the ultrasonic transducer elements 18 are disposed around a circumference of the distal opening 16 of the unit 10 and do not interfere with or obstruct the channel 15. The ultrasonic transducer elements 18 apply energy to the desired region of interest. The energy is received by the unit 10 and notably the different properties of the cortical and cancellous bones allow the unit 10 to discriminate between the cortical and cancellous bones in real time. The sensors 18 alternatively may be a magnetic sensor or another acoustic sensor known in the art. Various sensor configurations are possible and within the scope of the present disclosure.

Figure 2:
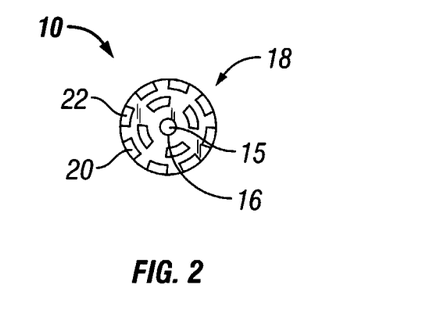
FIG. 2 is a front view of the hand held pedicle screw placement unit of FIG. 1, including a number of sensors.

The pedicle screw placement unit 10 has the sensors 18 disposed in an array. The array of sensors 18 is shown in FIGS. 1 and 2 and has a first sensor element 20 at a first circumferential position of the distal opening 16 with another second sensor element 22 of the array of sensors 18 at another second different circumferential position of the distal opening 16, and the remainder of sensors disposed in a likewise manner. In this manner, none of the sensors 18 obstruct the channel 15.

Figure 3:
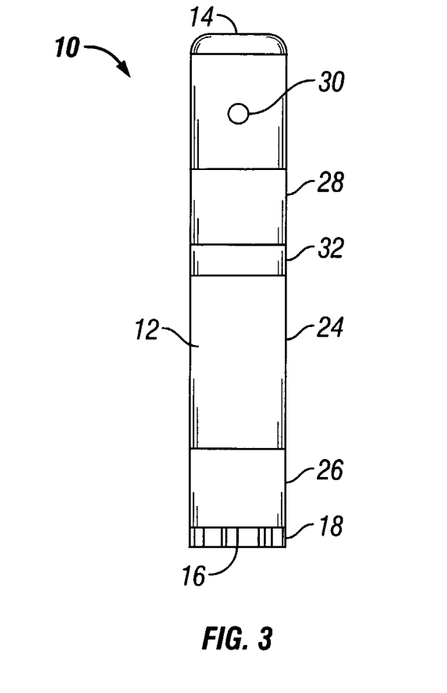
FIG. 3 is a top view of the hand held pedicle screw placement unit of FIG. 1 with an alarm.

Referring now to FIG. 3, the pedicle screw placement unit 10 also has a power source 24. The power source 24 preferably is any portable power source known in the art. The power source 24 is preferably any commercially available nickel cadmium or lithium ion batteries that may provide power to operate the unit 10 and also be disposable at the conclusion of the surgical procedure. Due to the sterile environment of the operating room during surgery, it is preferred that the unit 10 be fully disposable after use on a single patient. Alternatively, the sensing unit 18 with ultrasonic transducer elements may be cleaned, sterilized and reused, with a replaceable pre-sterilized battery pack 24 for each surgery. Although less preferred, it is contemplated that other sources of power may be used. For example, the power source 24 may be connected by a power cable to the sensing unit 18. However, even if a power cord is used, the channel 15 having the openings 14, 16 should be maintained.

The pedicle screw placement unit 10 also has a preamplifier unit 26. The preamplifier unit 26 is connected to the power source 24 and is also connected to the number of ultrasonic transducer elements 18. The preamplifier unit 26 preferably has a filter. The filter is configured to reduce any electronic noise from the signal that is received by the number of ultrasonic transducer elements 18. The preamplifier 26 amplifies the filtered signal and is coupled to a controller 28. In this manner, the preamplifier 26 provides the filtered signal to the controller 28.

The controller 28 is a digital signal processing unit that is connected to the preamplifier 26. Alternatively, the controller 28 may be a field programmable gate array, or another commercially available processor. The controller 28 may be programmed with one or more preprogrammed data fields such as a surgical implant size, implant length and implant diameter. The controller 28 receives the filtered signal from the sensor 18, and is also connected to an alarm 30. The controller 28 has program instructions to determine whether the received filter signal from the sensor 18 is a non-homogenous bone mass or is a homogenous bone mass. If the received signal is non-homogenous bone mass, the controller 28 has program instructions to continue searching and instructs the sensor 18 to continue searching. If homogenous bone mass is determined by the controller 28, the controller 28 will then output a control signal to the alarm 30. The alarm 30 then notifies the surgeon that a homogenous bone region has been found and a suitable region to introduce the pedicle screw has been determined. One skilled in the art should appreciate that if the unit 10 is subsequently moved or disturbed, the alarm 30 will no longer sound. The unit 10 may further be operable to include a switch to toggle between surgical implant size modes such as between a first pedicle screw size and another second pedicle screw size.

The pedicle screw placement unit 10 further has an orientation unit 32. The orientation unit 32 may be any device known in the art to provide for a feedback of an acceptable degree of the orientation of the entire hand held unit 10 along axis A (shown in FIG. 1) relative to the bone surface. Notably, if the unit 10 has an improper attitude, angle or degree relative to the desired homogenous bone region, it is not desirable to apply the medical element that applies the pedicle screw into the homogenous bone region as the medical element, Kirschner wire, or drill bit may not enter the bone region at a desired or acceptable angle. The orientation unit 32 thus provides a second signal to the controller 28 that a proper orientation of the unit 10 has been achieved on the homogenous bone region and it is acceptable to introduce the medical element such as a "K" wire or a drill bit into the homogenous bone region.

Figure 4:
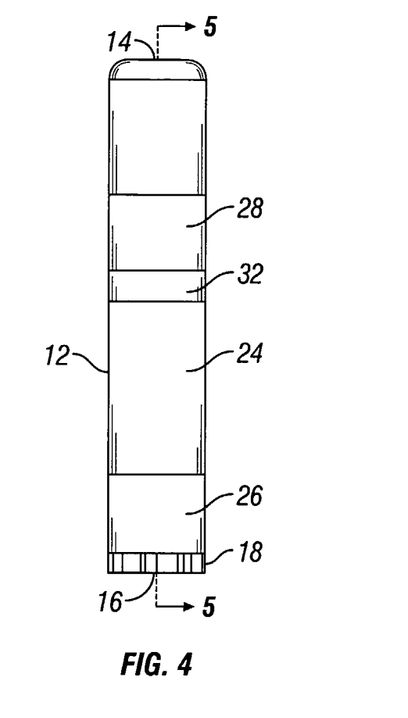
FIG. 4 is a bottom view of the hand held pedicle screw placement unit of FIG. 1.

Referring now to FIGS. 3 and 4, there is shown a top view of the pedicle screw placement unit 10. The pedicle screw placement unit 10 has a device 30 for identifying a homogenous bone region. The pedicle screw placement unit 10 in one embodiment preferably has the alarm 30 adjacent the proximal opening 14 of the unit 10. The alarm 30 is on an outer surface of the housing 12. Preferably, the alarm 30 is in a suitable location to readily alert the surgeon that the unit 10 is placed over a homogenous bone region. The alarm 30 is on an outer surface of the housing 12 however it is not limited to the location adjacent to the proximal opening 14. The alarm 30 may be placed in any location on the housing 12, such as, on the power source 24 shown in FIG. 4.

The alarm 30 is any signaling device known in the art to alert the surgeon that the unit 10 is placed over a homogenous bone region and that the region is suitable for introducing the pedicle screw. In one embodiment, the alarm 30 may be an audible alarm. The alarm 30 may emits an acoustic sound when the unit 10 is placed over or on the homogenous bone region. In another embodiment, the alarm 30 may emit a first tone and then modulate the first tone to a second tone when the unit 10 is placed in homogenous bone region.

Alternatively, the alarm 30 may be a visual alarm. The visual alarm 30 may be one or more light emitting diodes. The light emitting diode of the alarm 30 may modulate from a first condition to a second condition when the unit 10 is placed over the homogenous bone region. In one embodiment, the light emitting diode of the alarm 30 may blink when the unit 10 is placed in homogenous bone region. Alternatively, the light emitting diode of the alarm 30 may modulate from a first color to a second color when the unit 10 is placed over the homogenous bone region such as from red to green, or from yellow to red. The green color may indicate that the unit 10 is placed in the homogenous bone region. In another embodiment, the visual alarm 30 may further comprise a display such as a liquid crystal display. The display may further display a textual message such as "ready," "fire", or "orientation proper" or another similar message to alert the surgeon that the unit is placed in homogenous bone region. The alarm 30 may display another parameter of the surgical procedure. The display may further alert the surgeon to other information or parameters such as numerical information (i.e. minimum distance to the bone surface, spinal canal, etc.).

In still another embodiment, the unit 10 may have the alarm 30 with a tactile response mechanism alone or in combination with an acoustic or visual alarm. In this embodiment, the surgeon may feel a slight vibration to indicate the unit 10 is placed in homogenous bone region. Alternatively, the unit 10 may vibrate and terminate vibration when the homogenous bone location has been identified. The unit 10 may have a vibratory device that is connected to the controller 28. The controller 28 in response to a favorable reading will actuate the vibratory device to indicate to the surgeon that the medical element such as a drill bit, or "K" wire is ready to be introduced, and/or that the orientation of the unit 10 is acceptable. In still yet another embodiment, the alarm 30 may be a combination of visual, tactile and audible alarms. Various configurations are possible and within the scope of the present disclosure.

Figure 5:
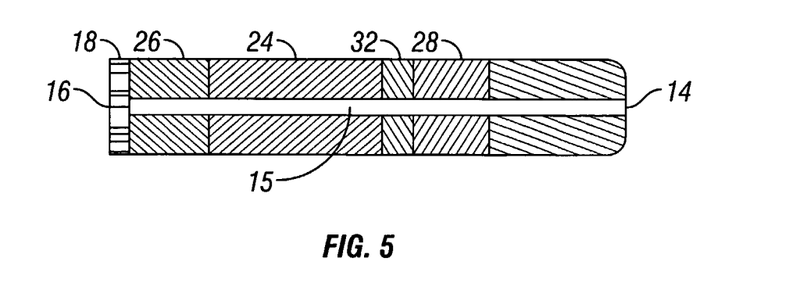
FIG. 5 is a cross sectional view of the hand held pedicle screw placement unit along line 5-5 of FIG. 4 showing a channel therein.

Referring now to FIG. 4, there is shown a rear view of the unit 10 having a number of ultrasonic transducer elements 18. As shown, the ultrasonic transducer elements 18 do not obstruct the channel 15 that traverses through the unit 10. Referring now to a cross sectional view of the unit shown as FIG. 5 along line 5-5 of FIG. 4, there is shown the channel 15 of the unit 10. The channel 15 is generally shown as cylindrical in shape and is suitably sized to allow a desired medical element such as a bone punch, a drill bit or "K" wire to traverse through the unit 10 without damaging the unit 10 and be applied to the desired homogenous bone region. Various types of implants or medical elements may be used with the present disclosure and include a titanium screw, a pin, a pedicle screw, a hip pin, a suitable spine construct such as a splint or cast, a metal implant, a ceramic implant, a polymer, a biocompatible implant, intramedullary nails, hip screws, trauma screws one or more Kirschner wires or so called "K" wires, a bone punch, a drill bit, a surgical drill, a vertebroplasty apparatus, a kyphoplasty apparatus, and any combination thereof. As can be understood from FIG. 5, the desired implant, such as a "K" wire, is introduced thorough the proximal opening 14 of the unit 10 and through the channel 15 and then through the distal opening 16 to introduce the implant to the desired homogenous region once the alarm 30 (FIG. 3) sounds. As can be understood, the coaxial introduction of the surgical implant (such as a Kirschner wire) through the channel 15 of the unit 10 provides the surgeon with significant advantages such as a real time feedback, precision and accuracy. In a further aspect of the embodiments, it is contemplated that an implant such as a pedicle screw may be cannulated so that the implant can be inserted over a "K" wire after insertion of the "K" wire through the device, such that the implant or other medical implement tracks over the K wire during insertion. It is contemplated that the unit 10 may not have to be removed from the desired located region during insertion of the implant if the available working space for a particular application is sufficient that the device may be sized to receive the implant or medical element therethrough.

As can be understood from the figures, the channel 15 extends through each of the number of components of the unit 10. Each of the number of components may be fitted with a snap fitting in order to removably connect to one another as shown. Moreover, each of the number of components has a suitable electrical coupling to connect with one another. The coupling is suitable to transmit signals from one component to another, such as from the preamplifier 16 to the controller 28.

Figure 6A:
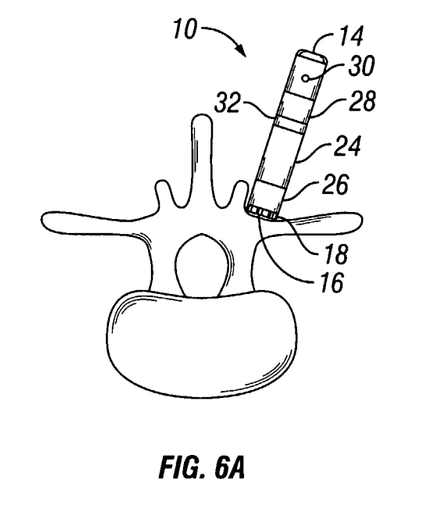
FIG. 6A is a first view of the pedicle screw placement unit being brought into contact with the outer surface of a bone.
Figure 6B:
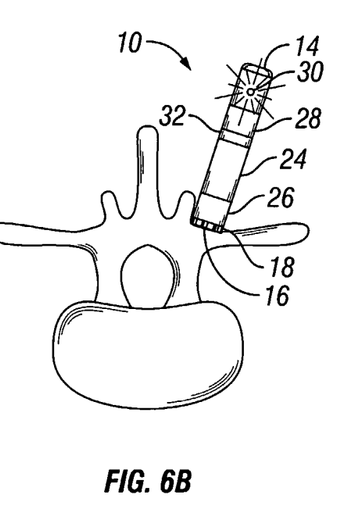
FIG. 6B shows the pedicle screw placement unit signaling the surgeon that an acceptable orientation and placement region has been determined.

Referring now to FIGS. 6A through 6C, there is shown the operation of the unit 10. Referring now to FIG. 6A, the unit 10 is sterilized, such as by using an ethylene oxide vapor and then placed over a desired bone surface that is to be treated. Optionally, a sterile gel or coupling media may be placed between the bone and the unit 10. As discussed herein, the controller of the unit 10 will determine an acceptable orientation of the unit 10 and region of the bone as the unit 10 is manipulated by the surgeon. Some of the variables that lead to an acceptable homogenous region for the application of the pedicle screw are a bone mineral density, bone thickness, bone histology, a bone disease or degeneration, bone water content, bone blood content, bone marrow content, bone cartilage composition or a combination of these factors. The sensors 18 will interrogate the pedicle and provide a signal to the controller 28 and the controller 28 determines a homogenous bone mass from the received signal. Referring now to FIG. 6B, once an acceptable homogenous bone region is determined, the alarm 30 will signal the surgeon and the surgeon will terminate movement of the unit 10. Optionally, the surgeon may also repeat the process and also consult some preoperative data to confirm the acceptable location of the homogenous bone region.

Figure 6C:
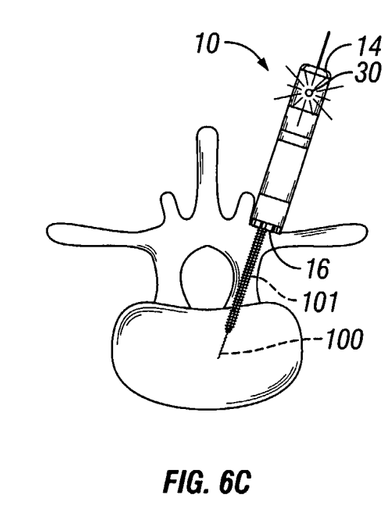
FIG. 6C shows a coaxial insertion of a "K" wire through the channel of the pedicle screw placement unit of FIG. 5 for insertion into the homogenous bone region with the pedicle screw placed over the "K" wire after insertion.

Referring now to FIG. 6C, once the homogenous bone region has been identified/confirmed, the surgeon will introduce the surgical implant 100, such as by introducing a so-called "K" wire, or other surgical implant through the proximal opening 14 of the unit 10 through the channel 15 and through the distal opening 16 to commence application in the homogenous bone region to prepare the site to receive a pedicle screw or other implant. Advantageously, introduction of the "K" wire is performed in a coaxial manner and without any removal of the unit 10 from the region for a real time identification of the homogenous bone region and correct placement of the "K" wire. In one embodiment in which a pedicle screw is to be placed in the spine, it is contemplated that the size of the pedicle screw having a diameter for a lumbar spine application is in a range that includes 5.5 mm to 6.5 mm is too generally large to provide a placement device with correctly placed transducers to be effective with the applicable anatomy and at the same time provide an open center of sufficiently large diameter to accommodate such a pedicle screw. In such a case, it is contemplated that the "K" wire would be placed through the device, the device removed leaving the K wire in place, and then inserting a cannulated implant over the "K" wire to track the "K" wire during implantation. In applications where the relative size of the implant and the anatomy can accommodate a device having a suitable arrangement of transducers, and an open center sufficiently large to receive the implant it is contemplated that the implant may be inserted through the device, with or without advance placement of a "K" wire. As shown in FIG. 6C, a cannulated pedicle screw 101 has been placed over a previously placed "K" wire 100. As will be appreciated from the disclosure, after placement of K wire 100 through the device into the desired bone, the device could alternatively have been removed and the implant shown in FIG. 6C as a pedicle screw could have been inserted over the "K" wire 100. Various configurations and reconstructive and therapeutic application are possible. The present disclosure is not limited to this specific embodiment. In another embodiment, the unit 10 may be used with other surgical implants that are suitably sized to be introduced through the channel 15. Such relatively narrower surgical implants or having a diameter less than about 6 mm may be introduced coaxially into the homogenous bone region directly through the unit 10. Such surgical implants may include any implant known in the art having a suitable narrow width to fit and traverse coaxially through the channel 15.

Figure 7:
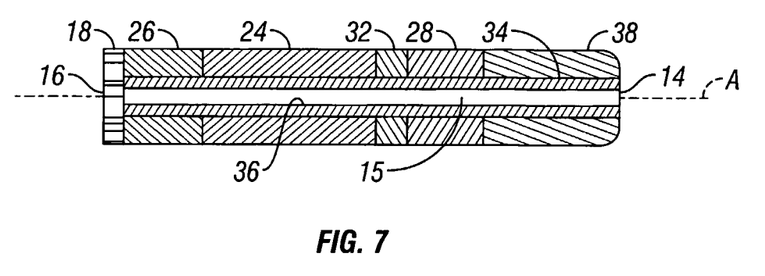
FIG. 7 shows a cross sectional view of another embodiment of the pedicle screw placement unit along line 5-5 of FIG. 4 with a sleeve.

In another embodiment of the present disclosure shown in FIG. 7, the unit 10 may further have a sleeve 34 that is coaxial with the channel 15. The sleeve 34 is a structure configured to receive the desired surgical implant such as a "K" wire and to provide structural integrity to the unit 10. The sleeve 34 may be a cylindrical shaped and be disposed parallel to the longitudinal axis A of the unit 10. The sleeve 34 may be a ceramic material, steel, or any other material with a high strength to protect the relevant components from the surgical implant application. Alternatively, the unit 10 may have an inner surface 36 of the channel 15 (with or without the sleeve 34) having a surface treatment. The surface treatment may increase a surface hardness and robustness of the inner surface 36 of the unit 10 during the procedure or during application of the surgical implant such as a "K" wire. The treatment preferably protects the various components of the unit 10. In one embodiment, the inner surface 36 may have a number of ceramic particles deposited in or on the inner surface 36. Alternatively, the inner surface 36 may have a number of metallic particles deposited in or on the inner surface 36. Moreover, the diameter of any sleeve 34 or channel 15 may be sized in order to provide a variety of sizes of the desired medical element such as a "K" wire, or another surgical implant. Further, a length of the unit 10 may also be modulated in order to accommodate the surgical implant.

Figure 8:
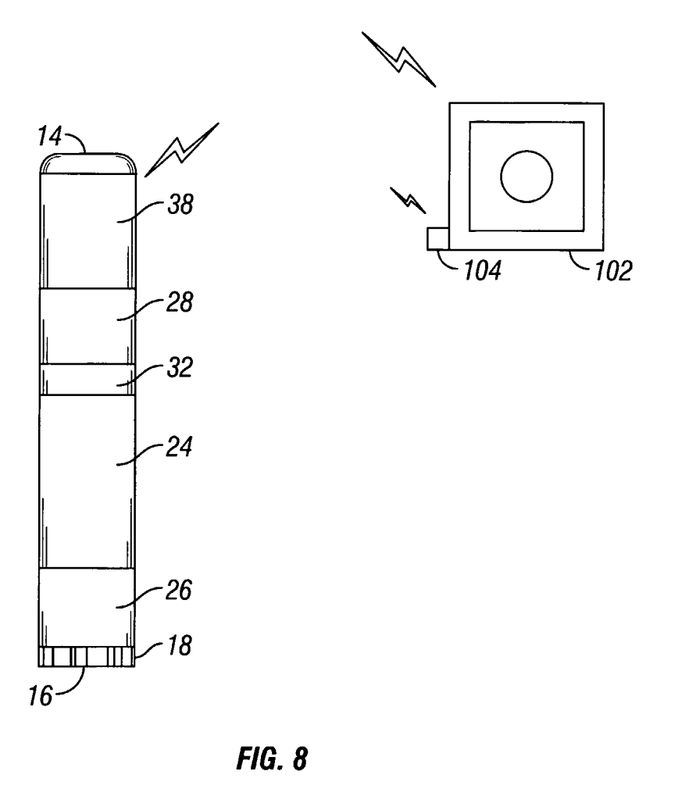
FIG. 8 shows a top view of another embodiment of the pedicle screw placement unit having a telemetry unit wirelessly communicating with a remote display unit.

Referring now to FIG. 9, in another alternative embodiment, the unit 10 may have a telemetry unit 38. The telemetry unit 38 may further comprise a discrete transmitter, a discrete receiver or a transceiver for emitting and receiving a wireless signal. The wireless signal may be received by a remote display device 102. The discrete transmitter/receiver or transceiver is coupled to the controller 28. In operation, the controller 28 may receive an input signal from the ultrasonic transducer elements 18. In response to the signal, the controller 28 may output a control signal to the transmitter/transceiver of the telemetry unit 38. The transmitter/transceiver of the telemetry unit 38 may then output a wireless signal to a remote receiver 104 that is connected to the remote display device 102. The remote display device 102 may then display one or more images of the bone region or one or more operating parameters of the surgical procedure for determining the desired homogenous region for insertion of the medical element such as a drill bit or a "K" wire. Some displayed operating parameters may include bone mineral density, bone thickness, bone histology, bone disease, bone degeneration, bone water content, bone blood content, bone marrow content, bone cartilage composition or a combination of these parameters. The display 102 may be a video monitor or graphical device and may have a discrete transmitter, a discrete receiver, or a transceiver 104 in order to wirelessly communicate with the unit 10. One skilled in the art should appreciate that the telemetry unit 38 may communicate using infrared transmission, radio frequency transmission, magnetic inductive transmission, or another method. Various configurations are possible and within the scope of the present disclosure. One skilled in the art should appreciate that the remote display device 102 may alternatively be connected by a suitable wired coupling to the unit 10. However, the coupling should be provided in a manner that does not affect the compact nature of the unit 10.

Although the present disclosure has been described with respect to particular embodiments, it will be readily apparent to those having ordinary skill in the art to which it appertains that changes and modifications may be made thereto without departing from the spirit and scope of the present disclosure.

What is claimed is:

1. A device for applying a medical element comprising:
   a housing defining a longitudinal axis having a channel being disposed therethrough, said housing having a proximal and a distal opening;
   at least one sensing device mounted to the housing adjacent said distal opening thereof;
   a signaling device mounted in said housing, the signaling device including a controller operatively connected to control the sensing device; and
   an alarm mounted in said housing, operatively connected to be controlled by the controller;
   wherein said at least one sensing device is configured and adapted to interrogate an external surface of a bone location for one or more variables of the cortical and cancellous bone of the bone location as the at least one sensing device is moved over the external surface of the bone location;

wherein said at least one sensing device is configured and adapted to generate a signal based upon the one or more variables of the cortical and cancellous bone of the bone location when positioned along the external surface of the bone location;

wherein said at least one sensing device is configured and adapted to output the signal to the signaling device;

wherein said signaling device is configured and adapted to provide an identification of a homogenous bone region and to activate and deactivate the alarm accordingly; and wherein the channel of the housing is configured and adapted so that a medical element can be applied to the homogenous bone location coaxially from said proximal opening through said channel and through said distal opening without removal of the device from the homogenous bone region wherein said at least one sensing device includes a plurality of ultrasonic transducer elements disposed around said distal opening.

2. The device of claim 1, wherein said housing is cylindrical.

3. The device of claim 1, wherein said alarm is disposed on an outer surface of said housing.

4. The device of claim 1, wherein said alarm is configured and adapted to emit an audible alarm.

5. The device of claim 1, wherein said alarm is configured and adapted to emit a visual alarm.

6. The device of claim 1, wherein said one or more variables of the bone location are selected from the group consisting of bone mineral density data, bone thickness data, bone histology data, bone disease data, bone degeneration data, bone water content data, bone blood content data, bone marrow content data, bone cartilage composition data, and any combinations thereof.

7. The device of claim 1, wherein the channel of the housing is configured and adapted so that the medical element can be applied to the homogenous bone region coaxially from said proximal opening through said channel and through said distal opening without removal of the device from the homogenous bone region to form a pedicular channel.

8. The device of claim 7, wherein the channel of the housing is configured and adapted to accommodate a medical element that is a drill bit.

9. The device of claim 1, further comprising a filter coupled to said at least one sensing device for removing noise from said signal.

10. The device of claim 1, wherein the alarm includes a vibration device for providing a tactile indication that said homogenous location has been determined.

11. The device of claim 1, further comprising a plurality of sensing devices positioned adjacent said distal opening.

12. The device of claim 1, wherein the channel of the housing is configured and adapted to accommodate a medical element that is a Kirschner wire.

13. A device for applying a medical element comprising:
a housing defining a longitudinal axis having a channel being disposed therethrough, said housing having a proximal and a distal opening;
at least one sensing device mounted to the housing adjacent said distal opening thereof;
a signaling device mounted in said housing, the signaling device including a controller operatively connected to control the sensing device; and
an alarm mounted in said housing, operatively connected to be controlled by the controller;
wherein said at least one sensing device is configured and adapted to interrogate an external surface of a bone location for one or more variables of the cortical and cancellous bone of the bone location as the at least one sensing device is moved over the external surface of the bone location;
wherein said at least one sensing device is configured and adapted to generate a signal based upon the one or more variables of the cortical and cancellous bone of the bone location when positioned along the external surface of the bone location;
wherein said at least one sensing device is configured and adapted to output the signal to said signaling device;
wherein said signaling device is configured and adapted to provide an identification of a homogenous bone region and to activate and deactivate the alarm accordingly;
wherein the channel of the housing is configured and adapted so that a medical element is can be applied to the homogenous bone region coaxially from said proximal opening through said channel and through said distal opening without removal of the device from the homogenous bone region; and
wherein said housing includes a surface treatment, said surface treatment being disposed in or on an inner surface of said channel wherein said at least one sensing device includes a plurality of ultrasonic transducer elements disposed around said distal opening.

14. The device of claim 13, wherein said surface treatment increases a surface hardness of said inner surface of said channel.

15. The device of claim 13, wherein said surface treatment comprises a sleeve adapted to protect said inner surface.

16. The device of claim 14, wherein said treatment comprises a plurality of material deposits in or on said inner surface of said channel.

17. The device of claim 14, wherein said material deposits are a plurality of ceramic particles.

18. The device of claim 14, wherein said material deposits are a plurality of metal particles.

19. The device of claim 15, wherein said sleeve is a ceramic sleeve.

20. The device of claim 15, wherein said sleeve is a metal sleeve.

* * * * *